United States Patent
Harding et al.

(10) Patent No.: US 7,547,382 B2
(45) Date of Patent: Jun. 16, 2009

(54) DETERMINATION OF PARTIAL FILL IN ELECTROCHEMICAL STRIPS

(75) Inventors: Ian Harding, Somerville, MA (US); Steven Diamond, Somerville, MA (US); Richard Williams, Andover, MA (US); Sridhar G. Iyengar, Salem, NH (US)

(73) Assignee: Agamatrix, Inc., Salem, NH (US)

(*) Notice: Subject to any disclaimer, the term of this patent is extended or adjusted under 35 U.S.C. 154(b) by 1008 days.

(21) Appl. No.: 10/907,813

(22) Filed: Apr. 15, 2005

(65) Prior Publication Data

US 2006/0231418 A1    Oct. 19, 2006

(51) Int. Cl.
G01N 1/00 (2006.01)
G01N 27/26 (2006.01)
G01N 31/00 (2006.01)
G01N 33/50 (2006.01)
G01N 17/00 (2006.01)
G01F 1/64 (2006.01)

(52) U.S. Cl. .................. 205/775; 205/792; 204/403.01

(58) Field of Classification Search ......... 204/400–420; 205/775, 777.5, 778, 778.5, 792; 324/662–664, 324/667, 671, 677, 678, 686, 425–437
See application file for complete search history.

(56) References Cited

U.S. PATENT DOCUMENTS

| | | | |
|---|---|---|---|
| 4,929,426 A | 5/1990 | Bodai et al. | |
| 5,160,278 A | 11/1992 | Johnson | |
| 5,243,516 A | 9/1993 | White | |
| 5,266,179 A | 11/1993 | Nankai et al. | |
| 5,320,732 A | 6/1994 | Nankai et al. | |
| 5,352,351 A | 10/1994 | White et al. | |
| 5,438,271 A | 8/1995 | White et al. | |
| 5,582,697 A | 12/1996 | Ikeda et al. | |
| 5,942,102 A | 8/1999 | Hodges et al. | |
| 5,997,817 A | 12/1999 | Crismore et al. | |
| 6,212,417 B1 | 4/2001 | Ikeda et al. | |
| 6,251,260 B1 | 6/2001 | Heller et al. | |
| 6,284,125 B1 | 9/2001 | Hodges et al. | |
| 6,287,451 B1 | 9/2001 | Winarta et al. | |
| 6,299,757 B1 | 10/2001 | Feldman et al. | |
| 6,475,372 B1 | 11/2002 | Ohara et al. | |
| 6,616,819 B1 | 9/2003 | Liamos et al. | |
| 6,743,635 B2 | 6/2004 | Neel et al. | |
| 6,856,125 B2 | 2/2005 | Kermani | |
| 6,872,298 B2 * | 3/2005 | Kermani | .................. 205/777.5 |
| 2002/0053523 A1 | 5/2002 | Liamos et al. | |

(Continued)

FOREIGN PATENT DOCUMENTS

EP    1312919 A2    5/2003

(Continued)

Primary Examiner—Kaj K Olsen
Assistant Examiner—Kourtney R Salzman
(74) Attorney, Agent, or Firm—Larson & Anderson, LLC

(57) ABSTRACT

Partial fill of an electrochemical test strip is determined by making a DC determination of double layer capacitance from charging or discharging charge on a test strip containing sample, for example a blood sample to be tested for glucose. The measured double layer capacitance is compared to a reference value. The double layer capacitance may be determined as an integral or differential capacitance. Double layer capacitance may also be used for quality control to monitor the quality of electrode formation, particularly in strips using screen printed electrodes.

17 Claims, 13 Drawing Sheets

U.S. PATENT DOCUMENTS

| | | |
|---|---|---|
| 2003/0098233 A1 | 5/2003 | Kermani et al. |
| 2003/0178322 A1 | 9/2003 | Iyengar et al. |
| 2005/0067301 A1 | 3/2005 | Morita et al. |
| 2005/0069892 A1 | 3/2005 | Iyengar et al. |
| 2005/0258034 A1 | 11/2005 | Iketaki et al. |

FOREIGN PATENT DOCUMENTS

| | | |
|---|---|---|
| EP | 1541998 A1 | 6/2005 |
| WO | WO 03/060154 A2 | 7/2003 |
| WO | WO 03/069304 A2 | 8/2003 |
| WO | WO 2005/022143 | 3/2005 |
| WO | WO 2005/022143 A2 | 3/2005 |

\* cited by examiner

DETERMINATION OF PARTIAL FILL IN ELECTROCHEMICAL STRIPS

BACKGROUND OF THE INVENTION

This application relates to a method for detecting partial fill in an electrochemical test strip, and to a meter, and meter-test strip combination for use in such a method.

Small disposable electrochemical test strips are frequently used in the monitoring of blood glucose by diabetics. Such test strips can also be employed in the detection of other physiological chemicals of interest and substances of abuse. In general, the test strip comprises at least two electrodes and appropriate reagents for the test to be performed, and is manufactured as a single use, disposable element. The test strip is combined with a sample such as blood, saliva or urine before or after insertion in a reusable meter, which contains the mechanisms for detecting and processing an electrochemical signal from the test strip into an indication of the presence/absence or quantity of the analyte determined by the test strip.

It is generally desirable in electrochemical test strips to utilize a small volume sample. One of the challenges that is encountered with small volume test strips is the occurrence of partial fill situations, where the volume of sample introduced to the strip is insufficient, resulting in erroneous readings. Various solutions to the problem of partial fill have been proposed.

In many instances, these solutions to the problem involve the use of additional electrodes. For example, U.S. Pat. No. 4,929,426 discloses the use of an impedance electrode that sample flows over when the analysis chamber is filled, while U.S. Pat. Nos. 5,582,697, 6,212,417, and U.S. 6,299,757 all disclose the use of a third electrode that can be used for fill detection. U.S. Pat. No. 6,743,635 discloses a four electrodes approach, including separate fill detect anode and cathode. U.S. Pat. No. 5,997,817 discloses a test strip with a window through which the sample can be viewed, and a "fill-to-here" line to assess sample sufficiency.

U.S. Pat. No. 6,856,125 discloses measurement of capacitance as a way to determine sample volume. The apparatus includes a sine wave generator to apply an AC signal to a biosensor cell containing a sample, a current-to-voltage converter, a phase shifter, a square wave generator, a synchronous demodulator, and a low pass filter which yields a signal proportional to the effective capacitance across the biosensor cell. This signal is proportional to the volume of the sample.

Because electrochemical test strips are generally disposable and multiple strips may be used by a diabetic in a single day, it is desirable to control the cost of each item. It would therefore be desirable to have a system for confirming the sufficiency of sample volume without significantly adding to the component count in the test strip or the meter, and hence the manufacturing cost of the test strip and meter. It would further be desirable if such a system were automated within the test meter, and did not depend on an observation or judgment made by the user.

SUMMARY OF THE INVENTION

The present invention provides an improved method for determining sample sufficiency that uses a measure of double layer charging or discharging between electrodes to determine the double layer capacitance of the test strip after sample addition. Double layer capacitance is proportional to the area of the electrodes that is wetted by sample, and thus provides a direct measure of the extent to which the sample chamber is filled. In accordance with the invention, partial fill can be detected in an electrochemical test strip having electrodes and a liquid sample disposed between the electrodes by a method comprising the steps of:

(a) introducing sample to an electrochemical test strip;
(b) applying a potential difference between the electrodes of the test strip;
(c) switching off the applied potential and optionally reapplying a second potential;
(d) observing current generated and determining from the observed current a double layer charging or discharging between the electrodes;
(e) observing a voltage change after the applied potential is switched off, and determining the double layer capacitance of test strip from the measured double layer charging or discharging and the observed voltage change; and
(f) comparing the determined double layer capacitance to a reference value, wherein a double layer capacitance less than the reference value is an indication that the liquid sample covers a portion of the facing electrodes and that the electrochemical test strip is only partially filled.

In one embodiment of the invention, double layer discharging is measured by (1) (1) applying a potential between the electrodes,
(2) (2) switching off the applied potential between the electrodes at a time $t_{switch}$;
(3) (3) monitoring the decay in the potential difference between the electrodes to identify the time, $t_{threshold}$, required for the potential to decay to a threshold value; and
(4) (4) determining the amount of double layer charge discharged during the interval $t_{switch}$ to $t_{threshold}$.

In another embodiment of the invention, double layer charging is measured by (1) (1) applying a first potential between the electrodes,
(2) (2) switching off the applied potential between the electrodes at a time $t_{switch}$;
(3) (3) monitoring the decay in the potential difference between the electrodes to identify the time, $t_{threshold}$, required for the potential to decay to a threshold value;
(4) (4) applying a second potential between the electrodes at $t_{threshold}$, whereby a current spike is generated;
(5) (5) determining the amount of double layer charging, as reflected by the area under the current spike; and
(6) (6) determining the double layer capacitance from the amount of double layer charging and the current at time $t_{switch}$.

The invention also provides a meter for use in association with an electrochemical test strip. The meter includes circuitry for applying a potential, monitoring current, switching potential off, and monitoring the decay in potential following the switching off of the potential. The meter may further include circuitry for monitoring current following re-application of the potential. Processors in the meter use the information generated to determine double layer capacitance, and to interrupt the measurement cycle if the value of double layer capacitance is insufficient. In addition, the meter includes circuitry for measuring the amount of analyte, for example glucose, present in a sample, and means for communicating the amount of analyte, or the termination of test due to insufficient sample volume to the user.

BRIEF DESCRIPTION OF THE DRAWINGS

The invention will be described with respect to a drawing in several figures.

DETAILED DESCRIPTION OF THE INVENTION

I. Definitions

Figure 1:
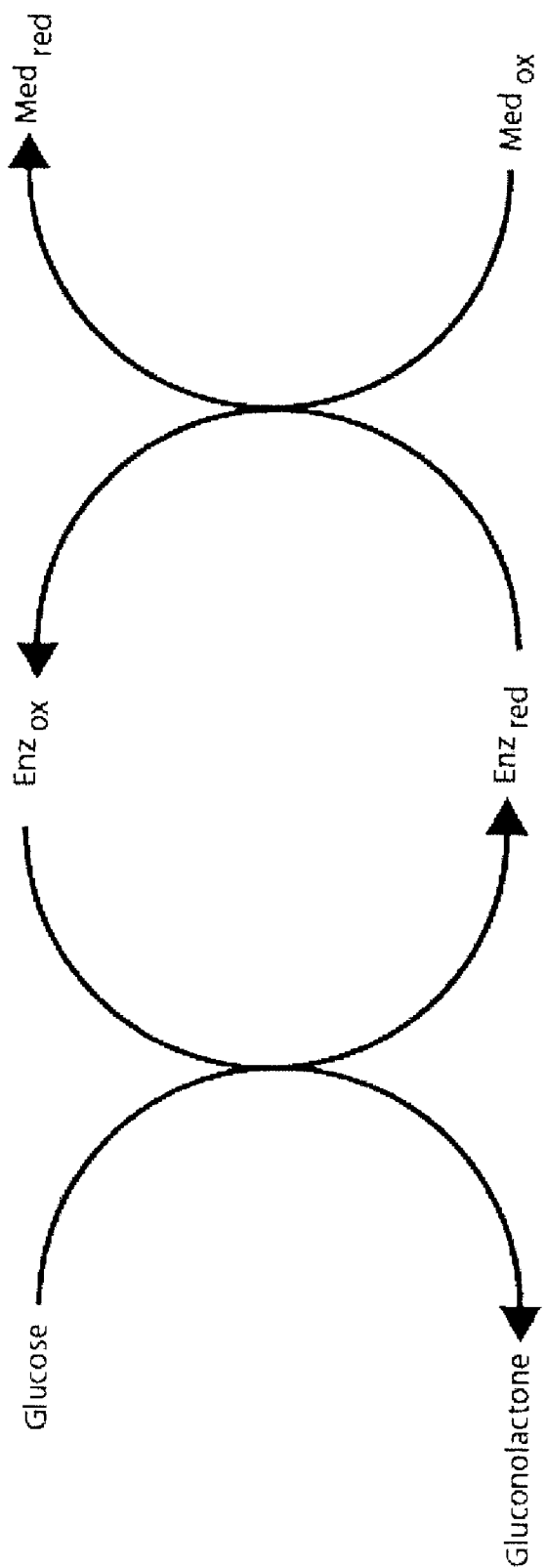
FIG. 1 shows the electron transfer reactions that occur in a conventional amperometric glucose detector.

As used in the specification and claims of this application, the following definitions should be applied:

(a) "analyte" refers to a material of interest that may be present in a sample. In the present application, the examples use glucose as an analyte, but the present invention is independent of both the type and amount of analyte. Accordingly, application to glucose detection systems should be viewed as merely a specific and non-limiting embodiment.

(b) "determination of an analyte" refers to qualitative, semi-quantitative and quantitative processes for evaluating a sample. In a qualitative evaluation, a result indicates whether or not analyte was detected in the sample. In a semi-quantitative evaluation, the result indicates whether or not analyte is present above some pre-defined threshold. In a quantitative evaluation, the result is a numerical indication of the amount of analyte present.

(c) "double layer" refers to the charged layers which form at a conductor/electrolyte interface as a result of adsorption of ions on the conductor surface causing a localized layer of neutralizing mirror charges in the conductor to form near the solid surface. The double layer is formed at each electrode in an electrochemical test strip when a liquid sample is present in contact with the electrode, whether or not a potential is applied. The amount of charge in a double layer, however, is a function of the electrode potential. The double layer structure behaves essentially as a capacitor.

(d) "double layer capacitance" is the capacitance of a double layer. It may be an integral capacitance, in which case it can be represented by the formula $C_{int}=I \Delta t/\Delta V$ or a differential capacitance, in which case it can be represented by the formula $C_{dif}=I/(dV/dt)$, where I is current, t is time and V is voltage. In some instances, the measured double layer capacitance is dominated by one electrode, for example, if one electrode has a substantially larger area, or where the adsorpoion of ions of one charge is stronger than ions of the other charge in the sample. In the case of glucose strips, the positive electrode is frequently dominant because of the greater ease with which negative ions, for example chloride ions, lose their hydration shell and are incorporated into the double layer. Double layer capacitance measured in these instances is within the scope of the invention, although care should be taken where one electrode is dominant that the geometry of filling is such that the double layer capacitance of the dominant electrode is representative of the fill-state of the electrochemical strip.

(e) "double layer charging" is the process of increasing the charge stored in a double layer as a result of an applied potential. The phrase "double layer charging at the electrodes" refer to charging at both electrodes or at a dominant electrode.

(f) "double layer discharging" is the process of decreasing the charge stored in a double layer as a result of switching off an applied potential. The phrase "double layer discharging at the electrodes" refer to discharging at both electrodes or at a dominant electrode.

(g) "electrochemical test strip" refers to a strip having at least two electrodes, and any necessary reagents for determination of an analyte in a sample placed between the electrodes. In preferred embodiments, the electrochemical test strip is disposable after a single use, and has connectors for attachment to a separate and reusable meter that contains the electronics for applying potential, analyzing signals and displaying a result.

(h) "facing electrodes" are a pair of electrodes disposed parallel to but in a separate plane from each other. Some or all of the opposed surfaces of a pair of facing electrodes overlap, such that potential gradients and current flows between the electrodes are in a direction substantially perpendicular to the opposed surfaces. Facing electrodes are distinguished from side-by-side electrodes in which the two electrode surfaces lie in the same plane, and in which potential gradients and current flow is substantially parallel to the surface of the electrodes. The present invention can be used with either facing or side-by-side electrodes, as well as other geometric arrangements.

(i) "switching off" of the applied potential refers to the creation of an open circuit that forces the current to be zero (by opening a switch or introducing a high impedance into the circuit) that allows a built-up chemical concentration gradient and ion adsorption in the double layer to determine the potential between the electrodes. This is not the same thing as setting the voltage to zero volts.

(j) "electrode resistance" causes a difference between the applied voltage, and the actual voltage perceived by the electrochemistry at the electrode. Electrode resistance arises as a result of the resistance of the electrode material and the connectors associated with the electrodes, fouling of the electrode and similar factors.

(k) $V_{drop}$ is the difference between the applied voltage and the actual voltage that arises as a result of electrode resistance.

(l) "oxygen carrying capacity" refers to the capacity of the sample to hold oxygen, in dissolved form and in a red blood cell reservoir.

(m) "$t_{mob}$" is a time determined experimentally during an analysis that reflects the mobility of mediator in a particular sample in a particular test cell. $t_{mob}$ is the time after the applied potential is switched off, that it takes for the potential between the electrodes to decay to a pre-determined value.

(n) "predetermined" is used in this application to refer to amounts or values that are determined empirically for a particular meter or test strip or meter/strip combination. The predetermined amounts or values will reflect an optimization for the needs of the user, taking into account the confidence levels needed, and need not achieve the best possible results or 100% accuracy.

II. Determination of an Analyte, for Example Glucose

Electrochemical detection of an analyte such as glucose is conventionally achieved by applying a potential to an electrochemical cell containing a sample to be evaluated for the presence/amount of glucose, an enzyme that oxidizes glucose, such as glucose oxidase, and a redox mediator. As shown in FIG. 1, the enzyme oxidizes glucose to form gluconolactone and a reduced form of the enzyme. Oxidized mediator reacts with the reduced enzyme to regenerate the active oxidase and produced a reduced mediator. Reduced mediator is oxidized at one of the electrodes, and electrochemical balance is maintained by a reducing reaction at the other electrode to result in a measurable current. The measured current is related to the amount of glucose in the sample, and various techniques are known for determining glucose concentrations in such a system. (See, for example, U.S. Pat. Nos. 6,284,125; 5,942,102; 5,352,2,351; and 5,243,516, which are incorporated herein by reference.)

Figure 2:
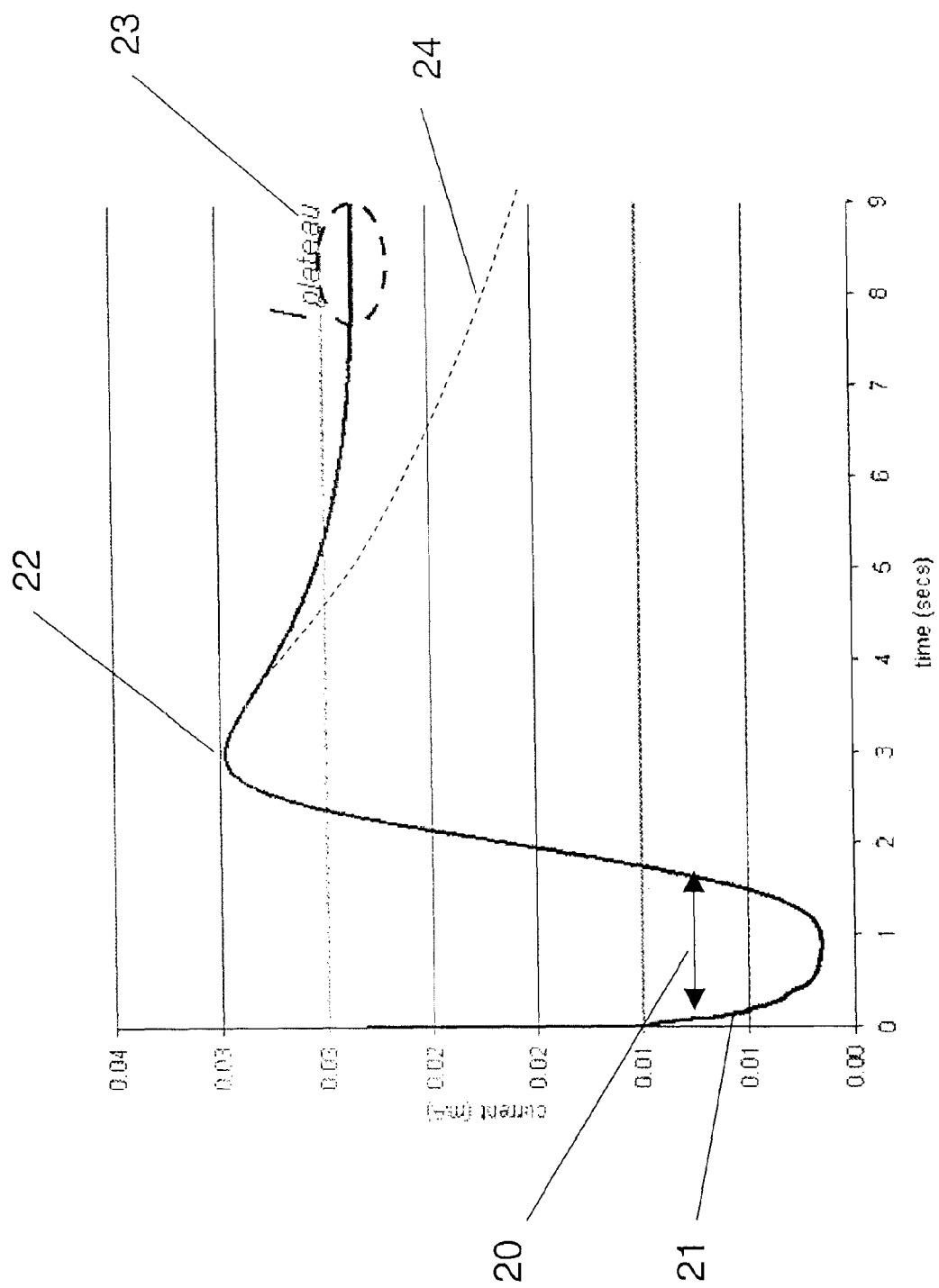
FIG. 2 shows a theoretical plot of current as a function of time after application of a potential in an electrochemical test strip for detection of glucose in which the test strip has facing working and counter electrodes, and the spacing of the electrodes is such that the recycling of mediator between the electrodes occurs.

FIG. 2 shows a theoretical plot of current, as a function of time after application of a potential in an electrochemical test strip for detection of glucose in which the test strip has facing working and counter electrodes, and the spacing of the electrodes is close together, such that recycling of mediator/charge carriers between the electrodes occurs, i.e., such that a shuttle current resulting from the oxidation and reduction of the mediator at the electrodes, independent of the presence of remaining analyte can be observed. The current trace shows an immediate initial current 21 on the time scale shown following application of the potential. This current is associated with the initial charging of the double layer and consumption of extraneous redox active species. Thereafter, the current decreases, because current is dependent on the mediator dissolving and then diffusing from the working electrode, where the reagents are deposited at the time of manufacture, to the counter electrode. The duration of this low current (indicated by arrow 20) is dependent on the rate at which the mediator dissolves, the distance between the electrodes and the effective distance that the mediator must travel to reach the counter electrode, and on the mobility of the mediator. Mediator mobility is a property of the mediator itself, i.e., the diffusion coefficient, but is also dependent on other sample properties such as hematocrit and viscosity. After the period of reduced current 20, the current rapidly rises to a peak current 22, and then gradually declines to a plateau current 23. Different approaches to glucose determination make measurements at different time points along this current profile. For example, U.S. Pat. No. 5,942,102 measures current in the plateau region. Cottrell analysis in the region between points 22 and 23 can also be utilized as described in U.S. Pat. Nos. 5,243,516; 5,352,351 and 6,284,125. In the present invention, any point in time can be used for purposes of determining the concentration of glucose or other analyte using amperometry.

In the embodiments described below where measurement of a charging charge is done with a second application of voltage, measurement of glucose or other analyte can be done during the initial voltage application, or based on a signal measured after the second application of voltage.

Determination of glucose or other analytes in a sample can also be made using other electrochemical techniques. These include potentiometry, for example as described in U.S. Pat. No. 6,251,260, which is incorporated herein by reference, or coulometry, for example as described in U.S. Pat. No. 6,299,757 which is incorporated herein by reference.

III. Determination of Double Layer Capacitance

Figure 13A:
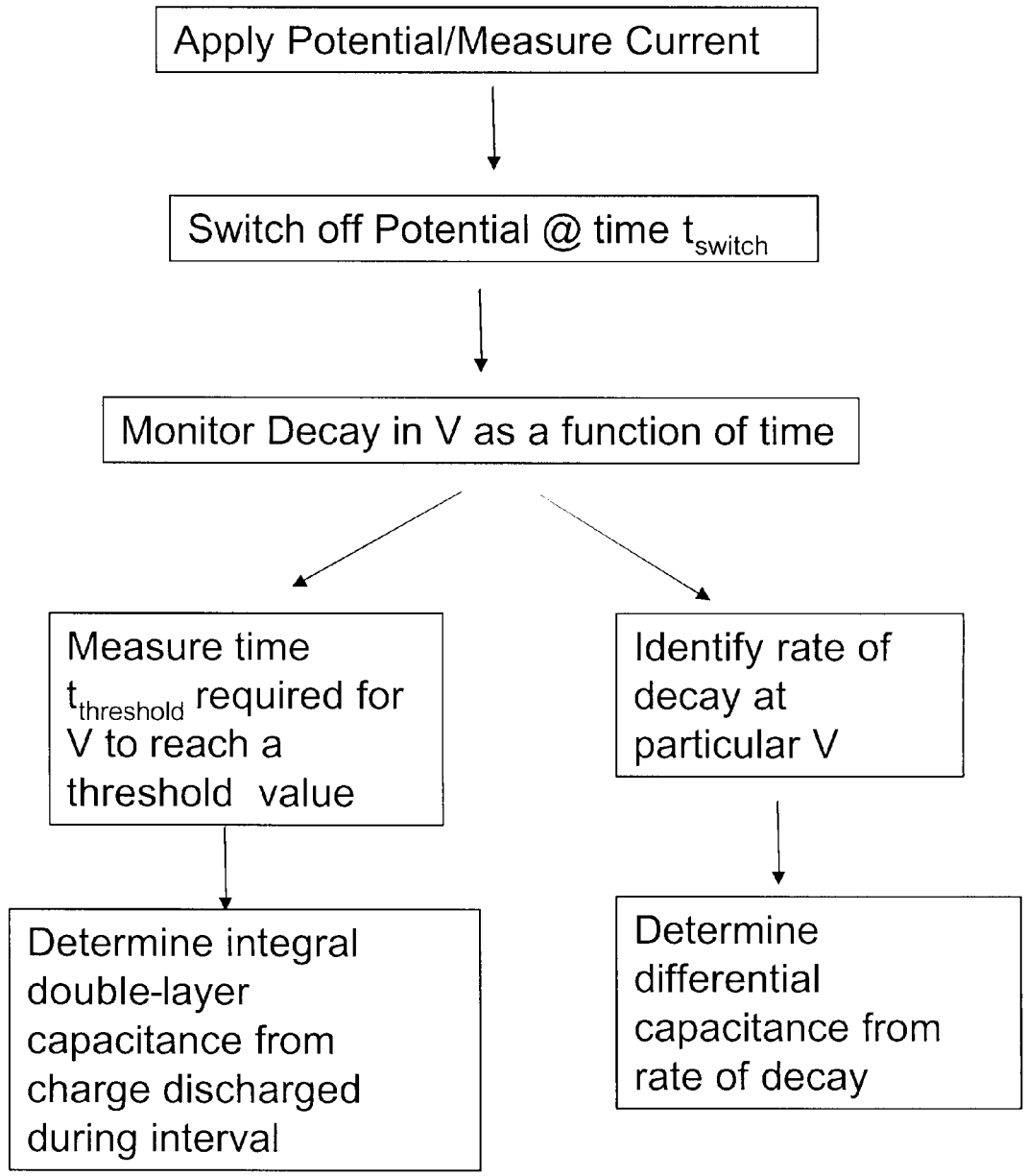
FIGS. 13A and B outline techniques for determining double-layer capacitance in accordance with the invention.
Figure 13B:
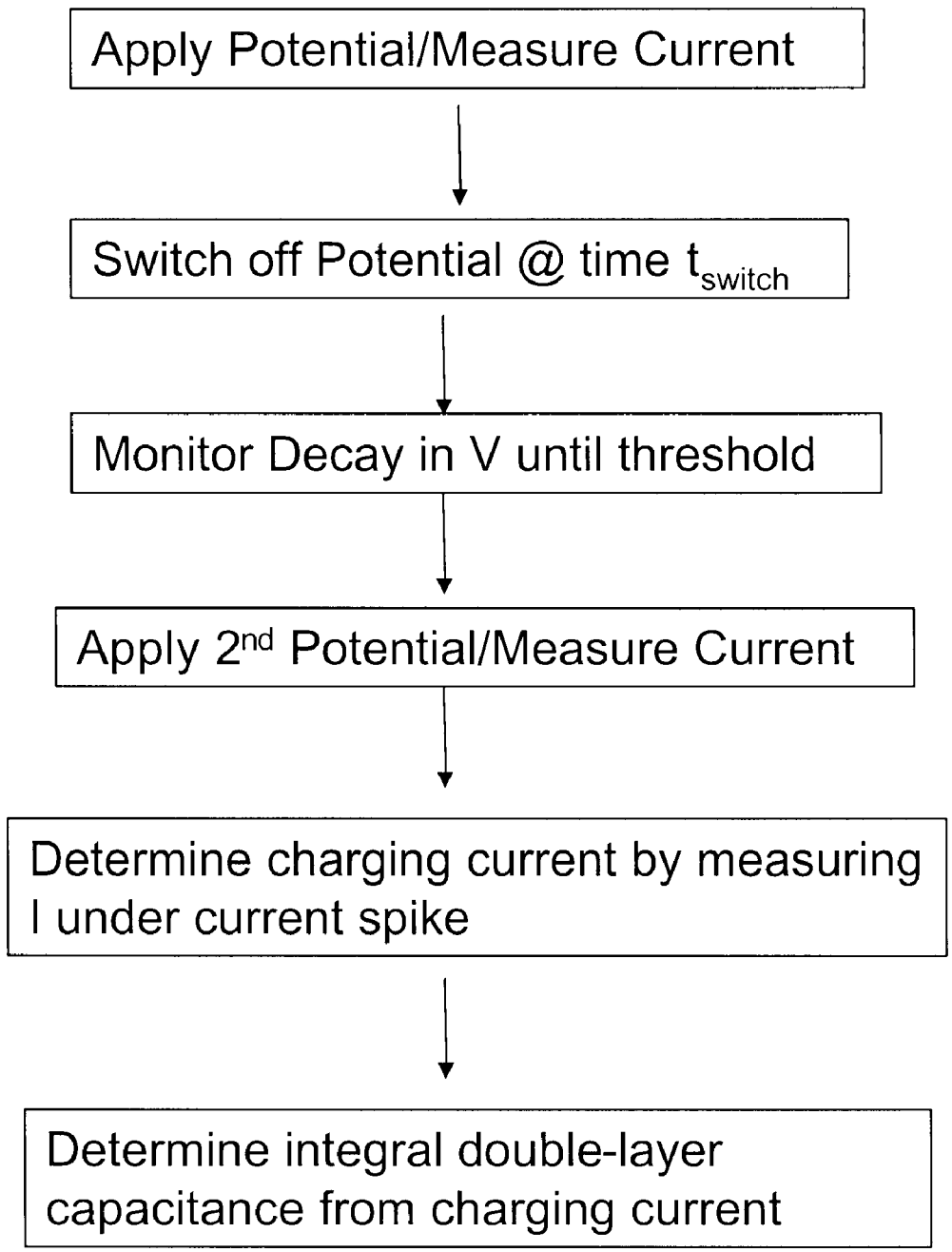

The present invention uses a determination of double layer capacitance to assess the sufficiency of sample volume introduced into an electrochemical test strip. Determination of double layer capacitance requires a knowledge of the current and the change in voltage as a function of time which can be obtained during either the charging or discharging of the double layer. Furthermore, the change in voltage can be viewed as a large, single-step change in voltage in which case an integral capacitance is obtained; or as a instantaneous change in voltage as a function of time, in which case a differential capacitance is obtained. Thus, double layer capacitance can be determined using any of three approaches which are summarized in FIGS. 13A and B. FIG. 13A summarizes determination of capacitance from discharge charge, while FIG. 13B summarizes determination of capacitance from charging charge.

A. Discharge Charge/Integral Capacitance

Figure 3:
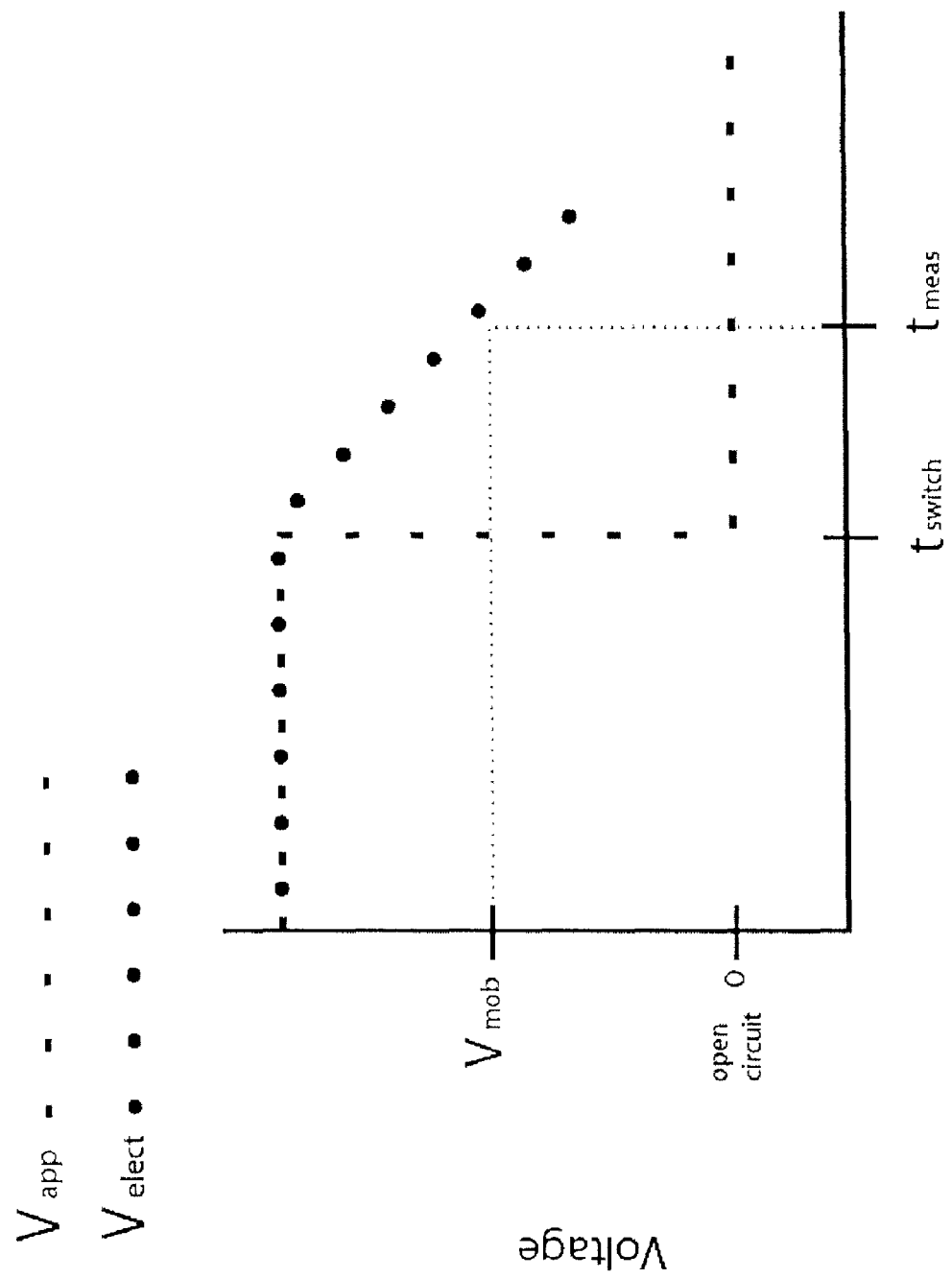
FIG. 3 shows a plot of the applied voltage, $V_{app}$, and the potential difference between the electrode, $V_{elect}$, as a function of time.

FIG. 3 shows a plot of the applied voltage, $V_{app}$, and the potential difference between the electrodes, $V_{elect}$ as a function of time. Initially, there is a constant voltage applied and a constant voltage at the electrode, and to a first approximation these two voltages are the same. At time $t_{switch}$, the applied voltage is switched off. At this point, $V_{elect}$ begins to decay. The decay is monitored until a pre-selected threshold voltage is reached, and the time, $t_{threshold}$ is noted. Integral capacitance is given by the formula:

$$C_{int}=I/(\Delta V/\Delta t).$$

In one embodiment of the invention, the I in this formula is the current just before $t_{switch}$, that is at a time before the voltage is switched off that is sufficiently close to $t_{switch}$ that the observed current is representative of the current in the instant prior to the voltage switch off. The actual time difference between the measurement and $t_{switch}$ can be on the order of 10 to 500 milliseconds, particularly if $t_{switch}$ falls in the plateau region where current is changing only slowly if at all. $\Delta V$ is the drop in voltage between the initial $V_{elect}$ which in a simple model may be assumed to be equal to the difference between $V_{app}$ and the threshold voltage $V_{threshold}$. $\Delta t$ is the difference between $t_{threshold}$ and $t_{switch}$. The capacitance determined in this way is related to the surface area of the electrodes or of the dominant electrode that is wetted by liquid sample such that a double layer can form.

Using a single value for I based on the current just before $t_{switch}$ is an approximation, but it is substantially valid when $t_{switch}$ occurs after the plateau region has been reached because change in I is small. Where greater accuracy is desired, however, or if $t_{switch}$ is at a time when I changes significantly over the time interval from $t_{switch}$ to $t_{threshold}$, then a more rigorous approach to determining I may be desirable. Although no current actually flows during the interval from $t_{switch}$ to $t_{threshold}$, $I_{threshold}$, the value that I would have had at $t_{threshold}$ if the applied voltage had been maintained, can be estimated using a linear model, a fit to a decay model such as the Cottrell equation, or some other extrapolation from the observed behavior prior to $t_{switch}$. A value of I that is half way between $I_{switch}$ and $I_{threshold}$, or a mathematical integration of a decay model can then be suitably used in the determination of $C_{int}$.

The value of $V_{threshold}$ is determined based on the value of $V_{app}$ as well as an expected time course for the decay. If $V_{threshold}$ represents a large portion of $V_{app}$, then the difference being measured is small, and the error is large. Further, as discussed below, in cases with resistive electrodes such as carbon electrodes there is an initial voltage drop, $V_{drop}$, associated with the electrode resistance, and $V_{threshold}$ must be lower than $V_{app}-V_{drop}$. On the other hand, if $V_{threshold}$ is too low, then the time to take the measurement is longer, which is generally less acceptable from a user perspective. To balance these two considerations, in the case of carbon electrodes $V_{threshold}$ is suitably at least 30 mV below $V_{app}$ and no lower than 60 mV, preferably no lower than 120 mV, and more preferably at least 150 mV. In one specific embodiment, using carbon electrodes for the measurement of glucose, $V_{app}$ is 300 mV and $V_{threshold}$ is selected as a voltage value between 150-240 mV.

B. Discharge Charge/Differential Capacitance

As an alternative to the determination of integral capacitance, differential capacitance can be determined from the discharge cycle. As in the case of determination of integral capacitance, the applied potential is switched off at time $t_{switch}$. At a measurement time thereafter, an instantaneous measurement of the slope of the voltage decay is determined. The time at which the measurement is made can be at a predetermined interval after $t_{switch}$ based on standard performance of a given strip design, for example between 1 and 500 msec after $t_{switch}$, or it may be determined based on the performance of the strip as it is used, in a manner comparable to taking a time measurement at $V_{threshold}$ as described above. This observation of the slope of the decay provide a value dV/dt. This is combined with a current measurement to produce a value for $C_{dif}$ in accordance with the equation $$C_{dif}=I/(dV/dt).$$

The value for I in this equation may be the value of the current just before $t_{switch}$ as described above, or it may be the projected value for the current at the measurement time, using any of the models described above.

One advantage to the determination of $C_{dif}$ as compared to $C_{int}$ arises because double layer capacitance is dependent on the voltage at which the capacitance is measured. Using $C_{dif}$, an instantaneous measurement can be taken at the same voltage every time, thus negating this source of variability.

C. Charging Charge/Integral Capacitance

Figure 4:
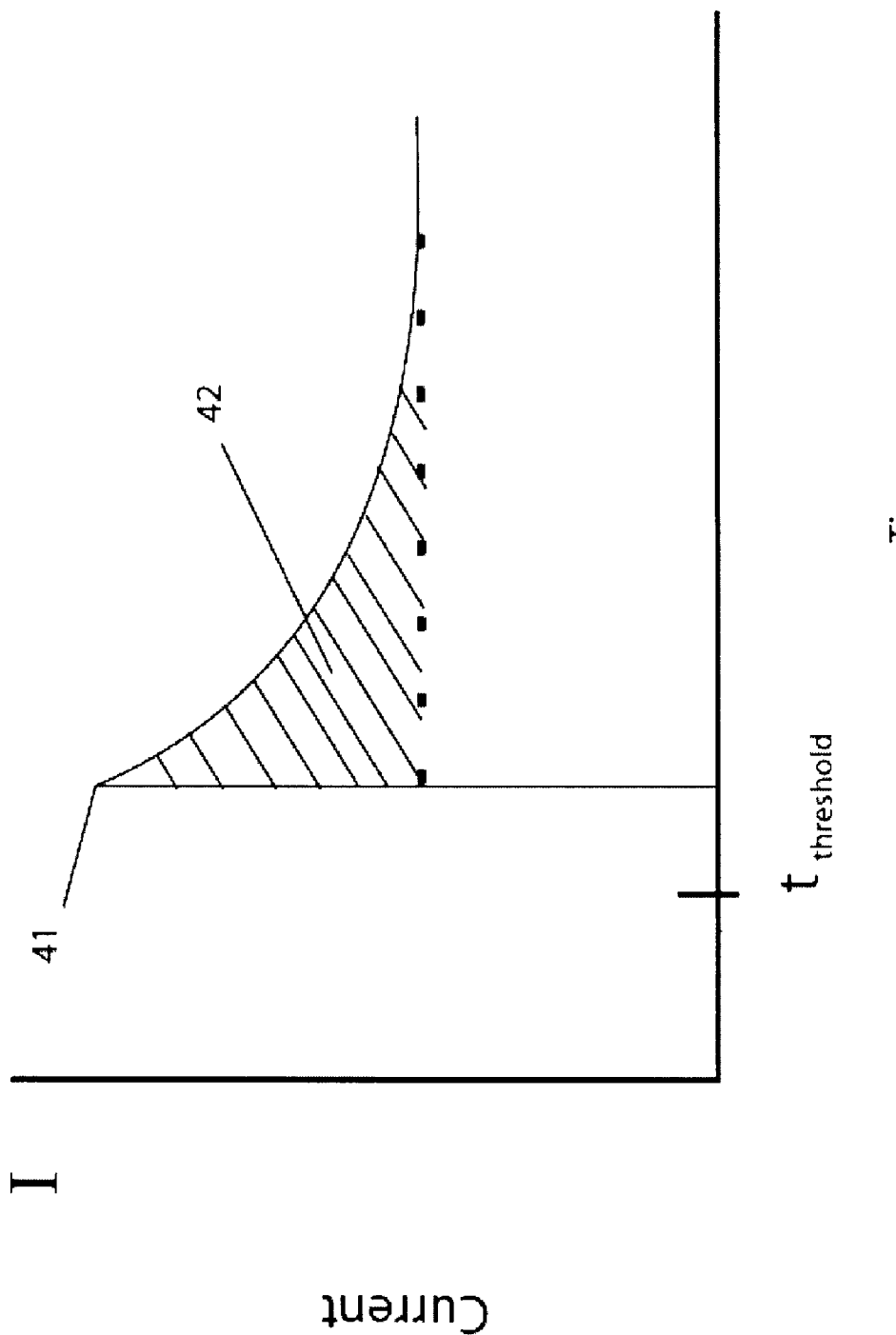
FIG. 4 shows a plot of current as a function of time when a potential is reapplied to the electrodes after $t_{threshold}$ is reached.

FIG. 4 shows a plot of current as a function of time, when a potential is reapplied to the electrodes after $t_{threshold}$ is reached. Following reapplication of the potential, there is a second current spike 41 followed by a decay to a current value that is essentially equal to the projected current from before the applied potential is turned off. The shaded area 42 under the current curve can be determined by integration of the signal, or a representative portion thereof, or using a triangular approximation, and is indicative of the charging of the double layer. Theoretically, the discharge charge measured as described above in A and this charging charge should be equal. In practice, experimental differences are observed, but the charging charge can nonetheless be used separately, or as a confirmation of the discharge charge as an assessment of partial fill.

In one embodiment of the invention, the voltage reapplied is the same as the voltage that is initially applied. However, the reapplied voltage may also be greater or smaller than the initially applied voltage, provided it restablishes the same diffusion limiting condition.

The time interval over which the current measurements are made may be established statically, that is fixed based on strip design, or dynamically. In the case of a static definition of measurement time, it is desirable to start measuring the current at a time after the current spike, for example 1 to 10 msec after, to eliminate effects of circuit response/saturation. The ending time for the measurement is then a predefined prior of time later, for example 100-1000 msec.

In a quasi dynamic approach, the end time may also be set as a multiple, for example an integer multiple, of Δt from the discharge phase. Thus, the measurement interval may be equal to Δt, or Δdt.

In a fully dynamic approach, the measurement time interval is determined based on characteristics of the measured current. In such cases, measurement can be made until a predetermined drop in the excess current ($I_{obs}-I_{switch}$) is achieved, for example more than 50%, preferably at least 75% and more preferably at least 90%, where $I_{obs}$ is the current observed at any given time after $t_{switch}$. Measurement can also continue until current has decreased to a level approaching $I_{switch}$, for example $1.1 \times I_{switch}$.

IV. Correction for Electrode Track Resistance

Figure 5:
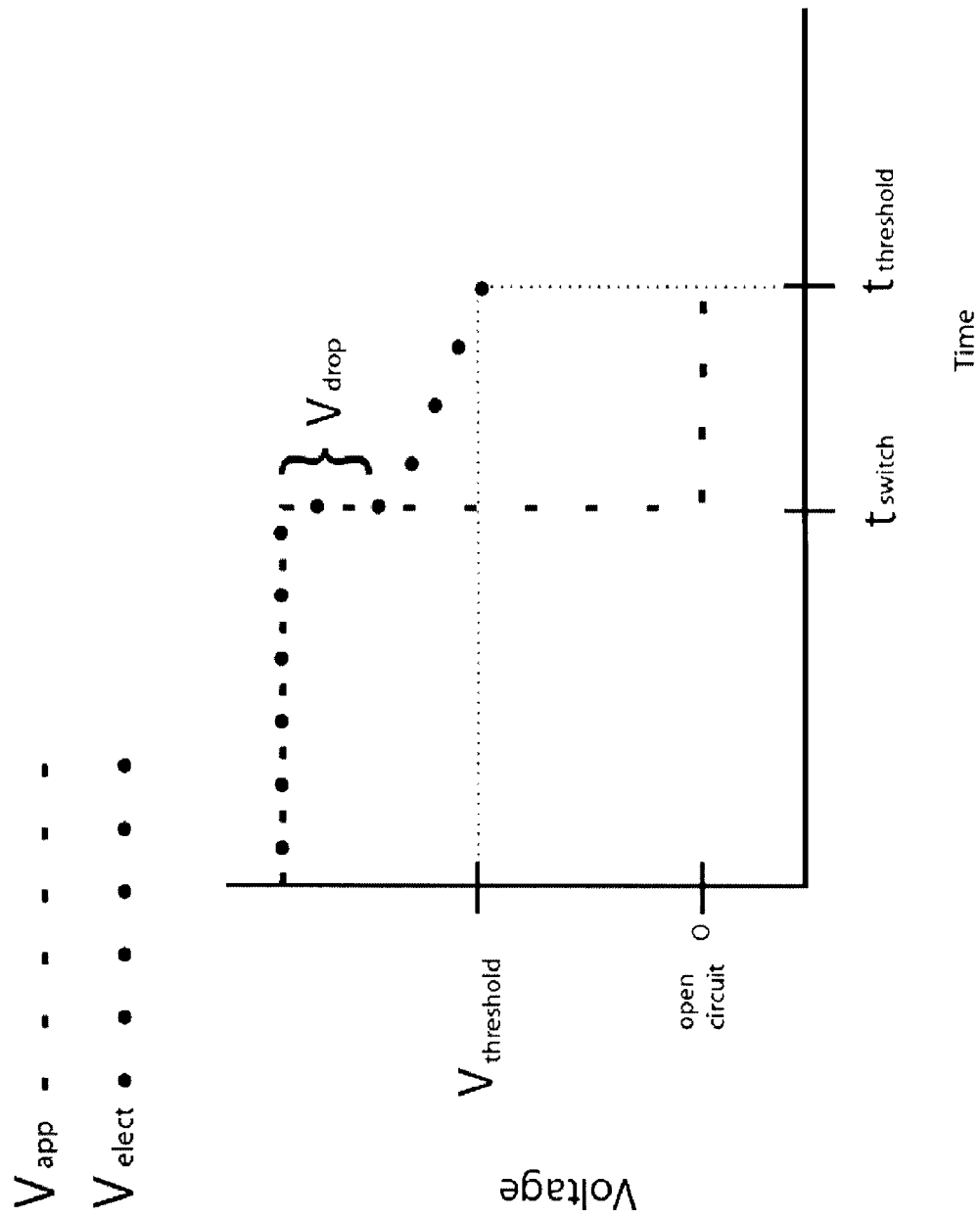
FIG. 5 shows a plot of voltage versus time, that illustrates the drop in voltage that occurs as result of electrode resistance.

When the actual voltage profile of an electrochemical strip with carbon electrodes is measured, an immediate drop in voltage is observed after the applied potential is switched off as illustrated in FIG. 5. The magnitude of this drop, $V_{drop}$ is a function of several factors, including the resistance of the electrode material and the connectors associated with the electrodes, fouling of the electrode and similar factors. Thus, the drop is larger with carbon electrodes than with a low resistance electrode such as one made of gold. In some embodiments of the present invention, the magnitude of $V_{drop}$ is taken into account in any of several ways.

In the case of determination of integral capacitance from the discharge charge, as described above, the selection of $V_{threshold}$ suitably depends on $V_{drop}$. Second, a more accurate indication of ΔV is provided by:

$$\Delta V=(V_{app}-V_{drop})-V_{threshold}.$$

In the case of determination of integral capacitance from charging charge, it is arithmetically convenient to set the second applied voltage to the first applied voltage plus $V_{drop}$ because then ΔV which should be the voltage actually applied to cause the new double layer charging, can be approximated, without measurement as the difference between the first applied voltage and the threshold voltage at which the potential is reapplied, and the only measured parameters are the decay time and the current.

In determining the differential capacitance, the voltage at which the measurement is taken can be described as (($V_{app}-V_{drop}$) minus a predetermined amount).

V. Correction for Temperature

In one embodiment of the invention, the value of double layer capacitance is corrected for the temperature of the sample, provided that the meter or the test strip is provided with means for determining this temperature. The temperature-corrected double layer capacitance, $C_{T-corr}$, can be represent by the formula $$C_{t-corr}=C_{DL}-T\text{-correction}$$

wherein $C_{DL}$ is the double layer capacitance as determined by any of the techniques outlined above.

The temperature correction term, T-correction, has the same form as described in commonly assigned U.S. patent application Ser. No. 10/907,803, filed Apr. 15, 2005, which is incorporated herein by reference, although in that application the correction term is used to correct the analyte concentration measurement.

The temperature correction term can be assessed by any technique that gives a measure of oxygen carrying capacity, in combination with a temperature measurement for the sample. The present inventors have found that a graph of measured raw analyte concentration versus a measure of oxygen carrying capacity is a line with a slope that is dependent on the temperature at which the measurements are made, but that is independent of $pO_2$ and glucose concentration over normal ranges of values. Changes in $pO_2$ or glucose concentration result in an additive offset of the graphed lines, but not a change in slope. A plot of this slope as a function of temperature can be used to define slope (S) and intercept (I) parameters that are combined into the temperature correction term for a given temperature T, in accordance with the equation:

temperature correction term=constant×[(S×T)+I]× OCC where OCC is a measure of oxygen carrying capacity such as hematocrit, and the constant is an empirically determined factor with a positive or negative sign.

Accuracy of the temperature correction factor can be improved when there is a large body of data gathered at one temperature and a limited body of data gathered at the measurement temperature by determining only the slope from the data gathered at the measurement temperature and determining the intercept from all of the available data. Thus, in the case where a large body of standard calibration data is available, the parameter I may be a constant established for the strip and meter combination, and only the slope need to be determined experimentally.

(a) Use of $t_{mob}$ as a Measure of Oxygen Carrying Capacity

In one embodiment of the invention, $t_{mob}$, a measure of the mobility of the mediator is used as the measure of oxygen carrying capacity. $t_{mob}$ is determined during the decay of the potential gradient following switching off of the potential. The decay in potential is monitored until the observed potential has decreased to a pre-determined value, $V_{mob}$. Decreases to around 50 mV are convenient where the applied voltage is on the order of 300 mV, although somewhat smaller values such as 47 mV or 48 mV may be found to provide optimum results in particular experimental configurations. In general, $V_{mob}$ is suitably 0.025 to 0.1V For example, in glucose determinations with a $V_{app}$ of 250 to 300 mV, $V_{mob}$ is suitably in the range of 25 to 100 mV, preferably 45 to 50 mV. $t_{mob}$ is the time is takes after $t_{switch}$ for this voltage to be reached.

Other ways of determining a measure of the rate of decay may also be employed. For example, an instantaneous slope of the decay of the potential can be determined, or the decrease in voltage over a predetermined time can be used. The meter may also select a particular time window and perform a linear regression on V versus log(t) or ln(t) to find $t_{mob}$ which is the time to a particular voltage. If the $V_{mob}$ does not fall within the selected window, a projection based on this linear fit can be used. The specific methodology is not critical, provided that the value of the measured decay is taken into account in determining the correction function.

(b) Use of Other Techniques as a Measure of Oxygen Carrying Capacity

U.S. Pat. Nos. 6,287,451 and 6,475,372, which are incorporated herein by reference, disclose electrochemical methods for determination of hematocrit in a disposable test strip. The hematocrit measurement is used in a multiplicative correction, as opposed to the additive correction of the present invention. The measurement can be used in both modes, however, just as $t_{mob}$ is used for both types of corrections as described above. This is because hematocrit is a measure of the red blood cells, and red blood cells have an oxygen carrying capacity.

In order to use any type of hematocrit measurement as a measure of oxygen carrying capacity in present invention, a series of calibration measurements are taken to obtain data point pairs of uncorrected analyte concentration and hematocrit at each of a plurality of temperatures. At each temperature, the data points are fit to a linear model and the slope of the line is determined. As noted above, this slope is independent of glucose and $pO_2$ such that while these parameters need to be kept the same across experiments, the particular values are not significant. The resulting slope/temperature data point pairs are then fitted to a linear model, to determine the slope and intercept which is incorporated into an additive correction factor as described above.

In some cases, the linear model may be sufficient only for a narrow range of the data. An improved additive correction factor may be determined for a wider range of temperatures or oxygen carrying capacities by introducing non-linear terms such as quadratic equations of exponents to terms.

VI. Dynamic Switching from Amperometric to Potentiometric Mode

In the present application, the meter first acts in an amperometric mode, and then after the applied potential is switched off, in a potentiometric mode. In order to enhance the quality and consistency of measurements made when operating in potentiometric mode, if is desirable to perform the switch to potentiometric mode only after a stable diffusion gradient of oxidized and reduced mediator has formed within the electrochemical test cell. In general, the potentiometry measurements will give the same stable reading at any point after the concentration gradients have formed a stable profile that extends "far enough" into the bulk of the sample.

To maximize the chances that stable diffusion gradients have been achieved, it is possible to simply establish a time after the start time of the measurement cycle at which the switch will be made. This time is determined empirically for a given test strip design, but may generally be on the order of 4 to 8 seconds. To allow the meter to accommodate a variety of different sample characteristics, however, $t_{switch}$ can be determined dynamically.

In one embodiment of the invention, $t_{switch}$ is determined dynamically from the determined value of $t_{peak}$ (the time of peak 22, in FIG. 2) by adding a time interval, for example 2 to 3 seconds to the determined value of $t_{peak}$.

In another embodiment of the invention, $t_{switch}$ is determined dynamically using a fixed value of $t_{switch}$ when $t_{peak}$ is small and $t_{peak}$ plus a predetermined amount when $t_{peak}$ is larger. For example $t_{switch}$ may have a fixed value of 3.5 second when $t_{peak}$ is less than 1.5 seconds, and be equal to $t_{peak}$ plus an offset (for example 2 second) when $t_{peak}$ is greater than 1.5 seconds.

In yet another embodiment, a third mode for measurement is established for circumstances when $t_{peak}$ occurs at times that are longer than ordinary. In this case, when $t_{peak}$ occurs above a predetermined threshold, for example 5 seconds, $t_{switch}$ is suitably determined as a function of $t_{peak}$ and an additive correction factor that uses predetermined constants derived from the slope of the Cottrell current.

Further, a maximum value of $t_{peak}$ can be established above which an error message is generated.

VII. Apparatus of the Invention

The method of the invention can be used with any strip that has facing electrodes, providing that a meter apparatus is provided that can receive the strip and provide the necessary applications of voltage and signal processing. Such a meter also forms an aspect of the present invention. Thus, the invention provides a meter for receiving an electrochemical test strip having electrodes and providing a determination of an analyte in a sample applied to the electrochemical test strip when received in the meter, said meter comprising
  (a) a housing having a slot for receiving an electrochemical test strip;
  (b) communications means for receiving input from and communicating a result to a user; and
  (c) means for making a DC determination of double layer capacitance on a test strip containing sample received within the meter, and comparing the determined double layer capacitance to a reference value, wherein a double layer capacitance less than the reference value is an indication that the liquid sample covers a portion of the electrodes and that the electrochemical test strip is only partially filled.

Figure 6:
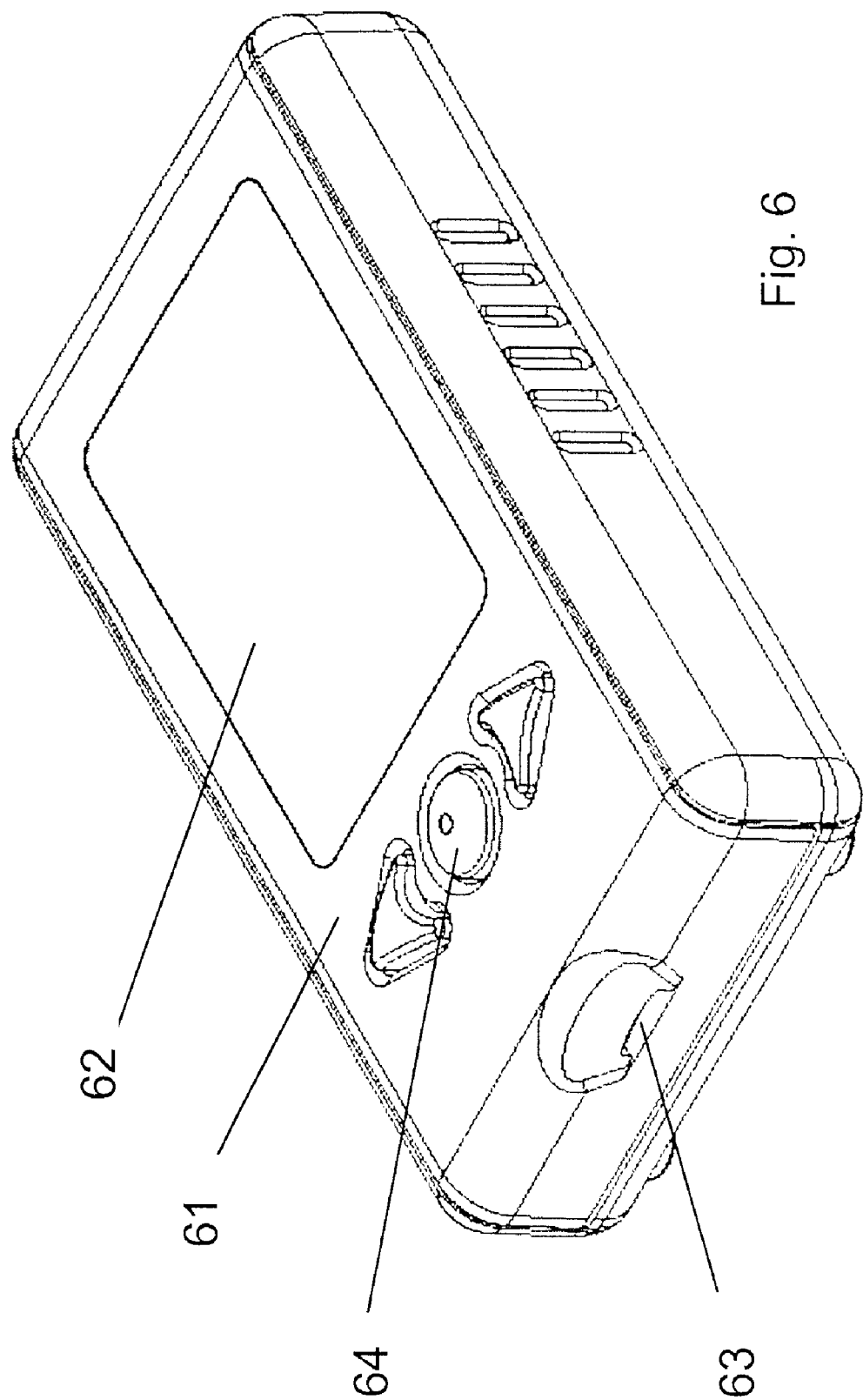
FIG. 6 shows an exterior view of a meter.

FIG. 6 shows an external view of a meter in accordance with the invention. The meter has a housing 61, and a display 62. The housing 61 has a slot 63, into which a test strip is inserted for use. The meter may also have a button 64 for signaling the start of the measurement cycle, or may have an internal mechanism for detecting the insertion of a test strip or the application of a sample. Such mechanisms are known in the art, for example from U.S. Pat. Nos. 5,266,179; 5,320,732; 5,438,271 and 6,616,819, which are incorporated herein by reference. In the meter of the invention, buttons, displays such as LCD displays, RF, infrared or other wireless transmitters, wire connectors such as USB, parallel or serial connections constitute means for receiving input from and communicating a result to a user, and can be used individually and in various combinations.

Figure 7:
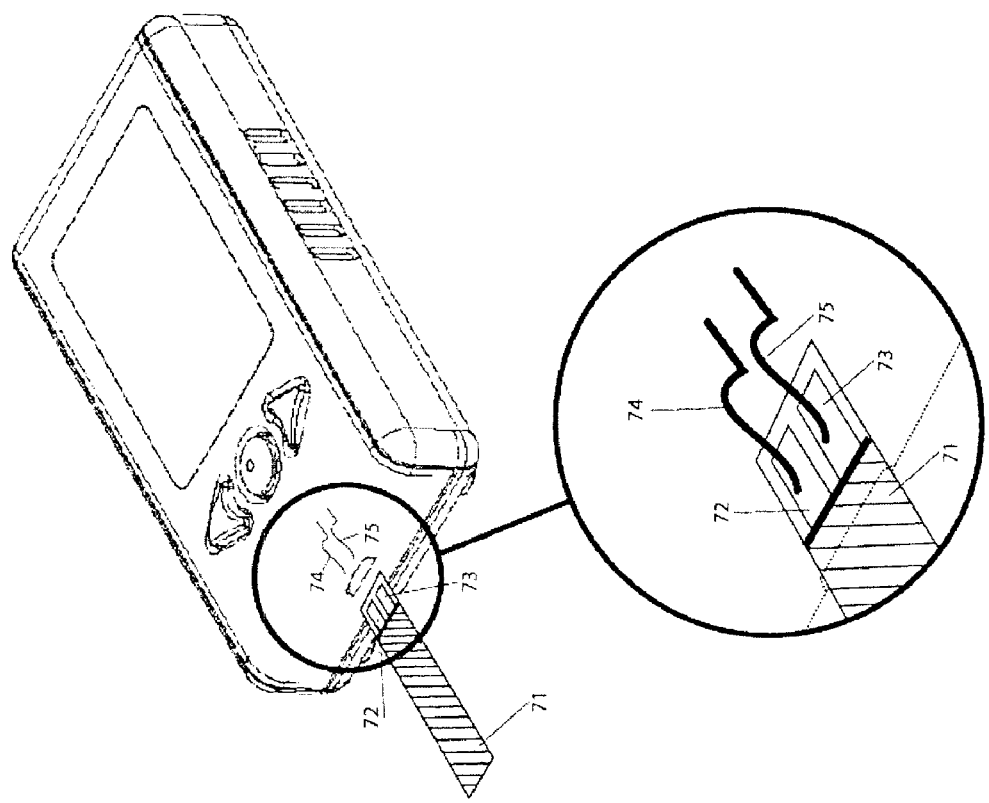
FIG. 7 shows connection of a test strip and connectors in a meter.

FIG. 7 shows an interior view in which the connection of the meter to a test strip is shown. As shown, the test strip 71 has contacts 72, 73 by which the electrodes are placed in electrical contact with contacts 74, 75 of the meter.

Figure 8:
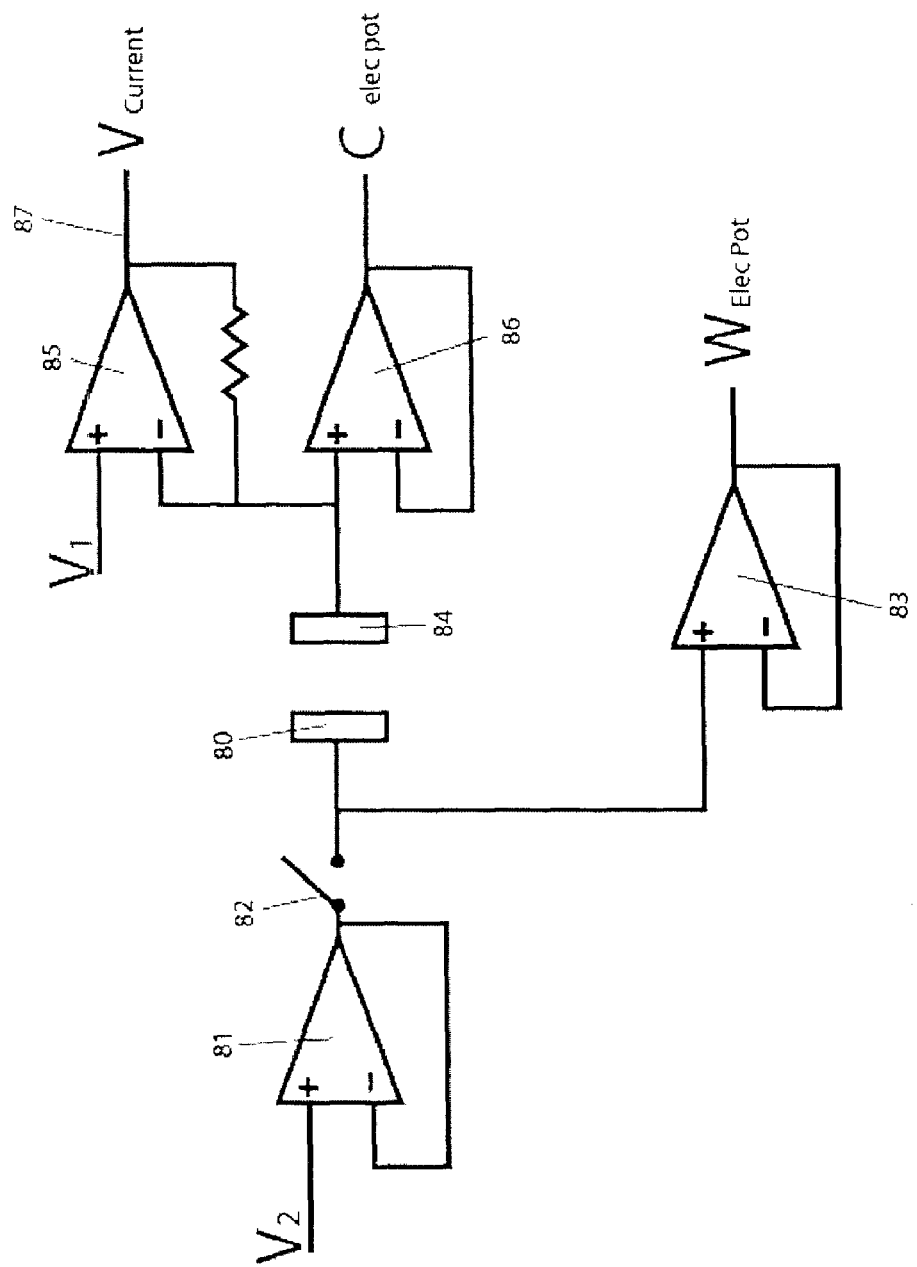
FIG. 8 shows a circuit diagram for switching between amperometric and potentiometric modes.

The means for making a DC determination of double layer capacitance comprises circuits, such as on a circuit board associated with a programmed microprocessor that interacts with the circuits to provide the desired switching between amperometric and potentiometric modes and to monitor current and voltage as described. Apparatus suitable for switching between an amperometric mode of operation in which current is measured and a potentiometric mode of operation in which a potential difference between the electrodes is measured are described in U.S. Provisional Applications No. 60/521,592, filed May 30, 2004, and 60/594,285 filed Mar. 25, 3005 which are incorporated herein by reference. FIG. 8 shows an electrical schematic of one embodiment of the meter of the invention. It will be appreciated, however, that other components can also be used, which achieve the same results in terms of applying and switching the voltage. Working electrode 80 is connected to op amp 81 via a connector containing switch 82, and to op amp 83. Counter electrode 84 is connected to op amps 85 and 86. Op amps 83, 85 and 86 are high impedance input amplifiers. When operating in amperometric mode to determine an analyte, a voltage $V_2$ is applied to op amp 81, and a voltage $V_1$ is applied to op amp 85, $V_2$ being greater than $V_1$. The resulting potential difference between the electrodes results in the generation of a current that is related to the amount of analyte, and this current can be monitored at output 87 and converted to an indication of the presence or amount of analyte. When switch 82 is opened to create an open circuit and stop application of the potential difference, current flow ceases, and the output of amplifier 86 assumes the potential of the counter electrode, while the output of amplifier 83 assumes the potential of the working electrode 80. The difference between the output from op amp 83 and op amp 86 indicates the decay in chemical potential and is processed in accordance with the methods described above to create an indication of partial fill.

Figure 9:
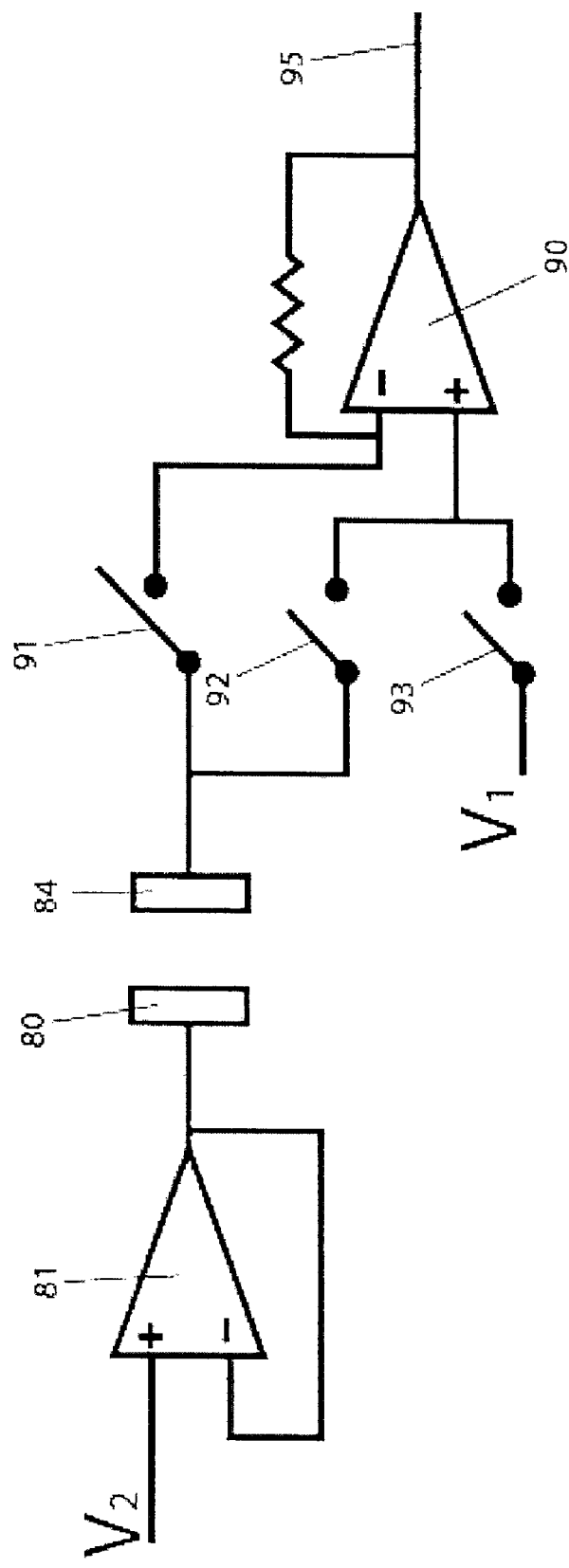
FIG. 9 shows a circuit diagram for switching between amperometric and potentiometric modes.

FIG. 9 shows an alternative version of this circuit using only two op amps and an increased number of switches. Working electrode 80 is connected to op amp 81 which received input voltage $V_2$. Counter electrode 84 is connected to high input impedance op amp 90 via one of two switched paths. Input voltage $V_1$ is connected to the circuit via a third switched path. When switch 91 and 93 are closed, and switch 92 is open, the circuit functions in amperometric mode, and the output at 95 reflects current flow at the electrodes. When switch 92 is closed, and switches 91 and 93 are open, the circuit operates in potentiometric mode and the output at 95 assumes the potential of the counter electrode (similar to amplifier 86 in FIG. 8). Thus, the output at 95 indirectly reflects the difference in potential between the electrodes. The actual difference in potential between the electrodes is the difference between the output at 95, and the output of op amp 81 (at 80, the working electrode).

In the meter of the invention, a signal to the user indicating incomplete fill is suitably generated when the measured value of the double layer capacitance is below the pre-determined level.

VIII. Quality Control Testing Using the Invention

As an alternative to indicating partial fill of an electrochemical test strip in use, the measured values of double-layer capacitance as described above also provides an indication of the quality of electrodes made using processes such as screen printing. Where the printing is of poor or inconsistent quality, the variation among the observed double-layer capacitance is larger than for a lot in which the printing quality is consistently good. (See FIG. 12 and Example 4). Thus, a further aspect of the invention provides a method for quality inspection of a lot of electrochemical test strips, comprising the steps of:
  (a) obtaining a plurality of test strips from the lot;
  (b) applying a sample to each of the test strips;
  (c) measuring the double-layer capacitance of the test strips in the presence of the sample; and
  (d) determining the variability in measured double-layer capacitance, wherein a variability in excess of a defined threshold indicates a quality deficiency in the test strips.

It will be appreciated that the "plurality" of test strips need to be a sufficient number to be representative of the lot as a whole, yet not so great as to result in destructive testing on an economically significant portion of the lot. Further, it is desirable to take test strips for this testing from different times within the preparation of the lot, and if multiple-strip sheets are made and then cut apart from different parts of the sheets.

The sample applied to the test strips could be a blood sample. However, as the measurement of double layer capacitance requires only the creation of a chemical potential gradient it is preferably a control solution containing a charge carrier, for example a mixture of ferrocyanide and ferricyanide.

The "variability" of the measured double layer capacitance can be determined using any acceptable mathematical analysis. For example, variability can be indicated by the range of measured values, or the standard deviation of the measured values.

IX. EXAMPLE

The invention will now be further described with reference to the following non-limiting examples. In these examples, measurements were made using electrochemical test strips having facing screen printed carbon electrodes, a nominal sample volume of 625 nanoliters, and a viewing window. A test strip was considered to be partially filled when sample could not be viewed through the viewing window. Blood samples used in the tests were freshly drawn (less than 8 hours old) using Vacutainer™ tubes, and were stabilized with EDTA as an anticoagulant. Blood samples with various hematocrits were prepared by centrifuging a normal blood sample of known hematocrit and glucose concentration, removing enough plasma to leave a hct 65 sample, and then creating lower hematocrits by recombining this sample with plasma in appropriate amounts. Because these samples were all prepared rapidly from a single blood sample, they all have the same plasma glucose concentration. Different glucose concentrations were generated by adding amounts of 1M glucose stock solution to blood prior to centrifugation.

Example 1

300 mV was applied to electrochemical test strips, and maintained until a plateau current was observed. The applied voltage was then switched off, and the potential difference between the working and counter electrodes was measured. Differential capacitance was determined for a plurality of samples having varying glucose concentrations (3.17 to 16.5 mM) and hematocrits (20, 40 or 60), at different potentials relative to the counter electrode. The results are summarized in FIG. 10. It should be noted that because the x-axis shows potential difference, the right hand side of the graph reflects measurements done at lower voltage drops.

Figure 10:
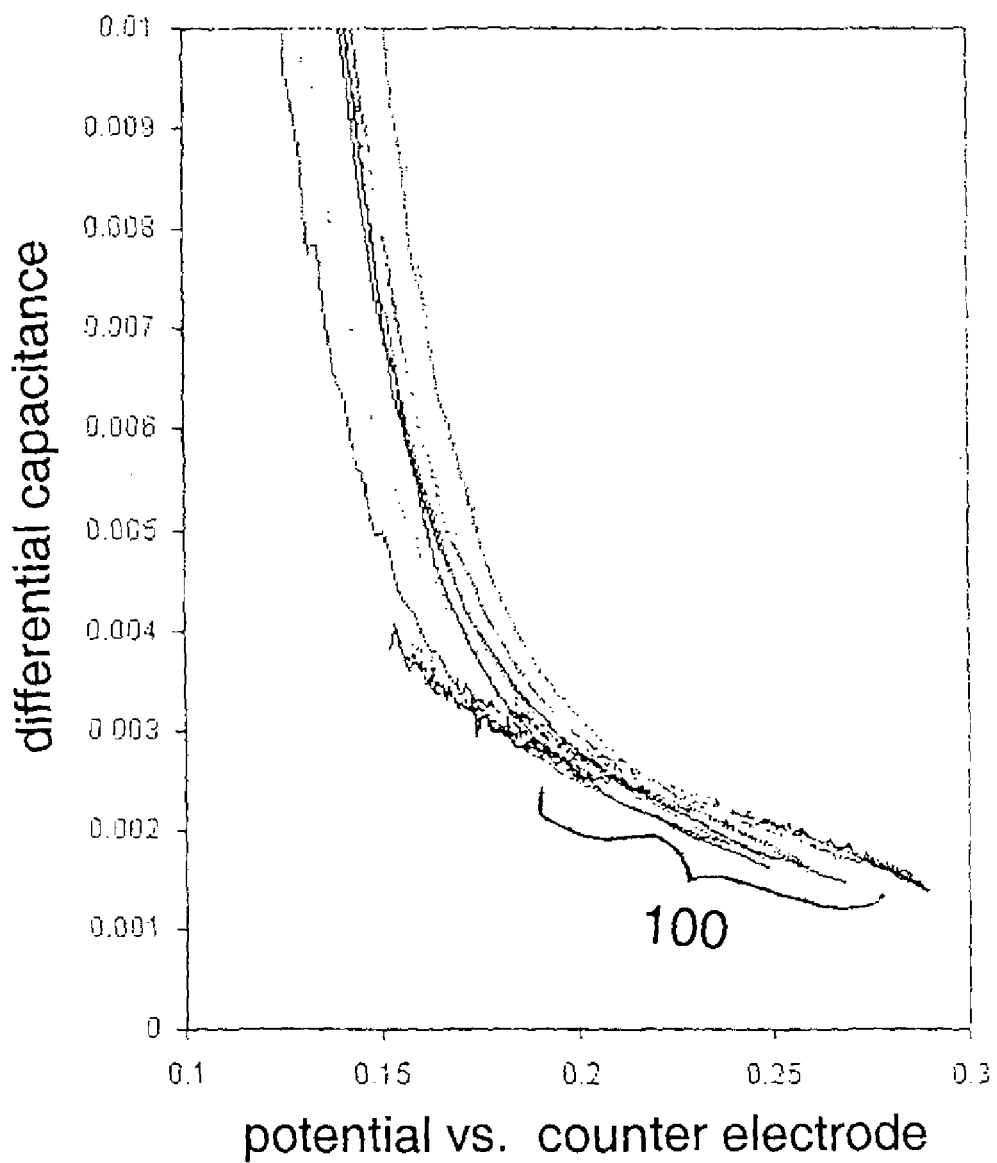
FIG. 10 shows the relationship between differential capacitance and potential.

As shown in FIG. 10, while the curves are not regularly dependent on concentration or hematocrit, the differential capacitance for a given sample/test strip varies significantly with the potential at which it is measured. Further, the graph shows a region 100 in which the change in $C_{dif}$ with voltage is less, and it is in this region of voltage difference in which measurements for determination of $C_{dif}$ are preferably made.

Example 2

300 mV was applied to electrochemical test strips with blood samples having either 2.79 mM or 20.2 mM glucose until a plateau current was observed. The applied voltage was then switched off, and the charge passed in discharging the double layer from 250 mV to 150 mV was measured. 300 mV was then reapplied, and the charge passed to recharge the double layer to 250 mV was observed. The relationship between the charging and discharging current was observed to be substantially linear with a zero intercept. However, the charge determined for recharging was lower than that for discharging, indicating that the measurement time of 100 ms was not sufficient for the recharging double layer to fully equilibrate with the solution. The observed amounts of charge were independent of glucose concentration, although the higher concentration decayed markedly faster.

Example 3

Figure 11:
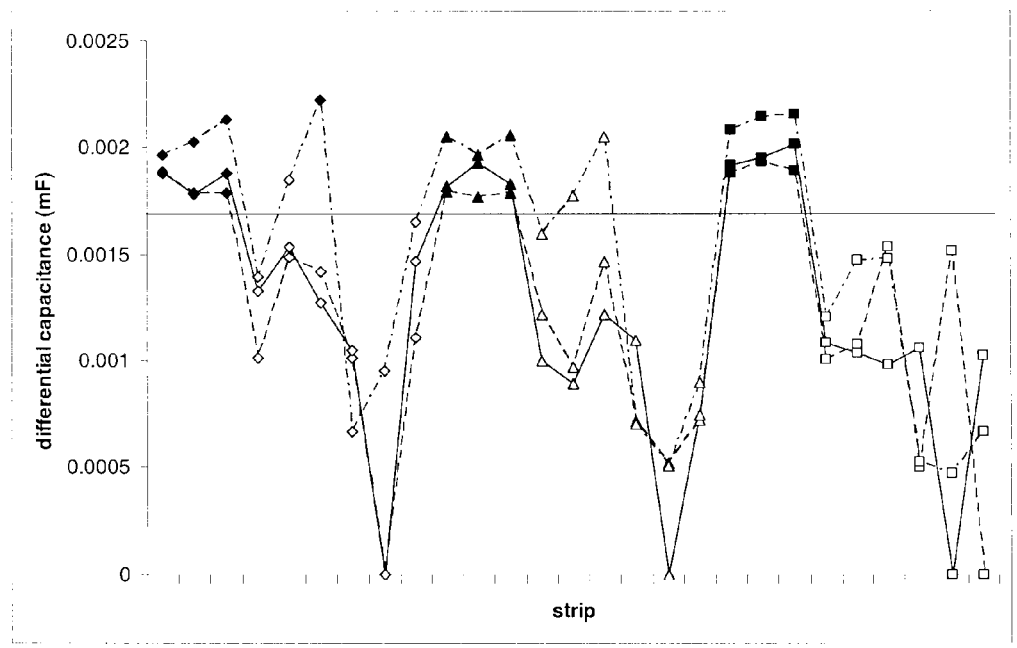
FIG. 11 shows measured differential capacitance for filled and partially filled strips.

300 mV was applied to electrochemical test strips with blood samples having varying hematocrit levels (20, 40, or 60) and glucose concentrations of 3.87 mM, 10.2 mM or 20.1 mM until a plateau current was observed. The applied voltage was then switched off and differential capacitance was determined at 40 mV below $V_{electrode}$. Strips were designated as filled or partial fill based on the observation of sample in the viewing window. FIG. 11 shows the measured differential capacitance for a variety of strips. In FIG. 11, the glucose concentration is indicated by line type (solid=3.87 mM, dashed=10.2 mM and dot-dash=20.1 mM); and the hematocrit by symbol shape (diamond=20; triangle=40; square=60). Filled symbols indicate filled test strips, while open symbols indicate partial fills. The horizontal line in FIG. 11 is a threshold level of differential capacitance set at 1.7 µF that could be used with this test strip in assessing sample sufficiency. As shown, all of the filled samples resulted in a capacitance above this threshold, while only three of the partial fills would have given a false acceptance.

It will be appreciated by persons skilled in the art that setting a threshold value depends on the willingness to accept a partial fill, or to exclude an otherwise acceptable sample.

Example 4

Figure 12:
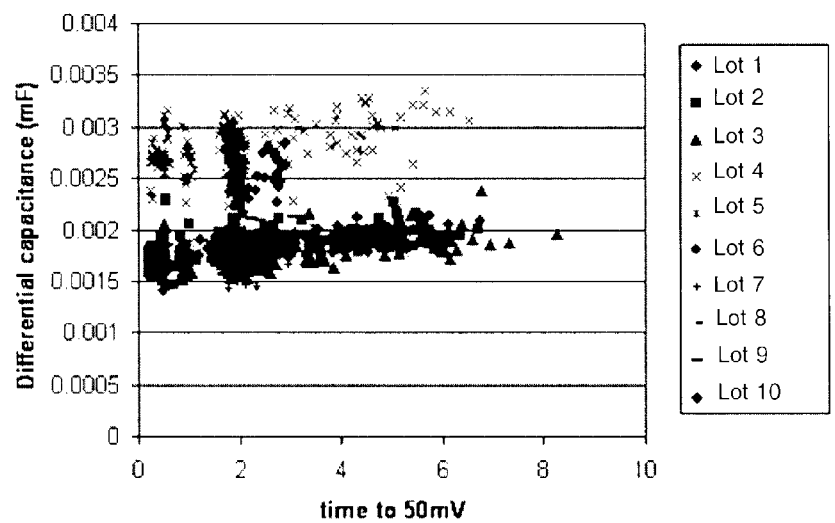
FIG. 12 shows lot-to-lot variation of differential capacitance as a function of time to 50 mV.

To evaluate the robustness of the method of the present invention, 10 different lots of test strips of the same design described above obtained from the same manufacturer were evaluated. FIG. 12 shows results for the ten lots, plotting differential capacitance versus time for a decay to 50 mV. Two things are observable from this graph. First, for 8 of the ten lots, differential capacitance is fairly constant, although the time to reach the 50 mV drop is variable. This argues in favor of dynamically determining the time of measurement, but exhibits the general robustness of the technique. The two lots that deviated from the other 8 also display a fairly constant level of capacitance, and very little variation in time to 50 mV. It was determined that in these lots the carbon electrodes were screen printed using a different technique. Thus, the cut off established for capacitance to account for partial fill can account for lot-to-lot variation with a consistent manufacturing technique, but may need to be reset where changes in manufacturing techniques are changed.

Those skilled in the art will have no difficulty whatsoever devising myriad obvious variations and improvements of the invention, none of which depart therefrom and all of which are intended to be encompassed within the claims which follow.

What is claimed is:

1. A method for detection of partial fill in an electrochemical test strip having electrodes and a liquid sample disposed between the electrodes comprising the steps of:
    (a) introducing sample to an electrochemical test strip;
    (b) applying a potential difference, $V_{app}$, between the electrodes of the test strip;
    (c) switching off the applied potential at time $t_{switch}$ and optionally reapplying a second potential;
    (d) observing current generated and determining from the observed current a double layer charging or discharging at the electrodes;

(e) observing a voltage change after the applied potential is switched off, and determining the double layer capacitance of test strip from the measured double layer charging or discharging and the observed voltage change; and (f) comparing the determined double layer capacitance to a reference value, wherein a double layer capacitance less than the reference value is an indication that the liquid sample covers a portion of the electrodes and that the electrochemical test strip is only partially filled.

2. The method of claim 1, wherein double layer capacitance determined is an integral capacitance determined in accordance with the formula:

$$C_{int} = I\Delta t / \Delta V,$$

wherein I is current, t is time and V is voltage.

3. The method of claim 2, wherein Dt is determined by monitoring the decay in the potential difference between the electrodes to identify the time, $t_{threshold}$ required for the potential to decay to a threshold value, $V_{threshold}$, and wherein $Dt = t_{threshold} - t_{switch}$.

4. The method of claim 3, wherein the amount of double layer charge discharged is determined as $$\text{charge} = I_{switch} \Delta t$$

where $I_{switch}$ is the current just before time $t_{switch}$.

5. The method of claim 3, wherein the current is an estimated value of current at time $t_{meas}$ determined by extrapolation from the observed current prior to $t_{switch}$.

6. The method of claim 3, wherein $\Delta V$ is the difference between $V_{app}$ and $V_{threshold}$.

7. The method of claim 3, wherein an immediate drop in voltage, $V_{drop}$, is observed following switching off of potential, and $\Delta V$ is given by $(V_{app} - V_{drop}) - V_{threshold}$.

8. The method of claim 2, wherein the observed current occurs after reapplication of a potential, and the double layer capacitance is determined from double layer charging.

9. The method of claim 1, wherein a differential capacitance is determined according to the formula:

$$C_{dif} = I/(dV/dt),$$

wherein I is current and (dV/dt) is the instantaneous change in voltage at time $t_{meas}$.

10. The method of claim 9, wherein the current I is the current just before time $t_{switch}$.

11. The method of claim 9, wherein the current is an estimated value of current at time $t_{meas}$ determined by extrapolation from the observed current prior to $t_{switch}$.

12. The method of claim 7, wherein $t_{meas}$ is determined dynamically.

13. The method of claim 12, wherein $t_{meas}$ is the time at which the observed potential is lower than the applied potential by a predetermined amount.

14. The method of claim 8, wherein an immediate drop in voltage, $V_{drop}$, is observed following switching off of potential, and wherein $t_{meas}$ is the time at which the observed potential is lower than $(V_{app} - V_{drop})$ by a predetermined amount.

15. The method of claim 14, wherein the current I is the current just before time $t_{switch}$.

16. The method of claim 14, wherein the current is an estimated value of current at time $t_{meas}$ determined by extrapolation from the observed current prior to $t_{switch}$.

17. The method of claim 1, wherein the measured double layer capacitance is corrected by an additive correction term that is a function of temperature and oxygen carrying capacity prior to comparison with the reference value.

* * * * *